| | | | |
|---|---|---|---|
| United States Patent [19] | | [11] Patent Number: | 4,960,921 |
| Suresh et al. | | [45] Date of Patent: | Oct. 2, 1990 |

[54] MULTIPLY PROMOTED MN-SB OXIDE CATALYSTS

[75] Inventors: Dev. D. Suresh, Macedonia; Robert K. Grasselli, Aurora; Frances I. Ratka, Cleveland Heights; James F. Brazdil, Mayfield Village, all of Ohio

[73] Assignee: The Standard Oil Company, Cleveland, Ohio

[21] Appl. No.: 478,382

[22] Filed: Feb. 12, 1990

Related U.S. Application Data

[60] Division of Ser. No. 904,587, Sep. 8, 1986, which is a continuation-in-part of Ser. No. 569,425, Jan. 9, 1984, abandoned, which is a continuation-in-part of Ser. No. 340,910, Jan. 20, 1982, abandoned, which is a continuation-in-part of Ser. No. 190,532, Sep. 24, 1980, abandoned.

[51] Int. Cl.$^5$ ............................................. C07C 253/26
[52] U.S. Cl. ..................................... 558/325; 558/321; 558/322; 558/323; 558/319; 562/523; 562/545; 568/455
[58] Field of Search ................ 558/325, 321, 322, 323

[56] References Cited

U.S. PATENT DOCUMENTS

| | | | |
|---|---|---|---|
| 3,282,982 | 11/1966 | Callahan et al. | 260/465.3 |
| 3,365,482 | 1/1968 | Khoobiar | 260/465.3 |
| 3,427,343 | 2/1969 | Callahan et al. | 260/465.3 |
| 3,546,138 | 12/1970 | Callahan et al. | 252/454 X |
| 3,595,911 | 7/1971 | Ball | 502/215 X |
| 3,662,016 | 5/1972 | Furuoya et al. | 502/202 X |
| 3,849,337 | 11/1974 | Manara et al. | 260/465.3 X |
| 3,879,435 | 4/1975 | Gasson et al. | 260/465.3 |
| 3,956,182 | 5/1976 | Ishimi | 502/211 X |
| 4,035,418 | 7/1977 | Okada et al. | 252/433 X |
| 4,148,757 | 4/1979 | Brazdil et al. | 502/204 X |
| 4,167,494 | 9/1979 | Grasselli et al. | 502/215 X |
| 4,290,920 | 9/1981 | Suresh et al. | 502/215 X |
| 4,311,611 | 1/1982 | Sasaki et al. | 260/465.3 |
| 4,316,856 | 2/1982 | Guttmann et al. | 502/214 X |
| 4,322,368 | 3/1982 | Guttmann et al. | 260/465.3 |
| 4,335,018 | 6/1982 | Franz et al. | 502/215 X |
| 4,388,223 | 6/1983 | Ferlazzo et al. | 502/215 X |

FOREIGN PATENT DOCUMENTS

| | | | |
|---|---|---|---|
| 274799 | 9/1965 | Australia | 260/465.3 |
| 41-11972 | 6/1966 | Japan | 260/465.3 |

*Primary Examiner*—Joseph Paul Brust
*Attorney, Agent, or Firm*—C. S. Lynch; D. J. Untener; L. W. Evans

[57] ABSTRACT

Certain novel multiply promoted Mn-Sb oxides are superior catalysts for the ammoxidation of olefins to the corresponding unsaturated nitriles, the selective oxidation of olefins to unsaturated aldehydes and acids, and the oxydehydrogenation of olefins to diolefins.

4 Claims, No Drawings

MULTIPLY PROMOTED MN-SB OXIDE CATALYSTS

This application is a division of application Ser. No. 904,587, filed Sept. 8, 1986, which is a continuation-in-part of application 569,425, filed Jan. 9, 1984, now abandoned which is a continuation-in-part of application Ser. No. 340,910 filed Jan. 20, 1982, now abandoned which is a continuation of Ser. No. 190,532 filed Sep. 24, 1980, now abandoned.

BACKGROUND OF THE INVENTION

The present invention relates to novel manganese antimonate catalysts for use in various oxidation-type reactions, such as the oxidation of olefins to produce aldehydes and acids, the ammoxidation of olefins to produce unsaturated nitriles and the oxydehydrogenation of olefins to diolefins.

U.S. Pat. No. 4,035,418, the disclosure of which is incorporated herein by reference, describes certain manganese antimonate catalysts which are useful in various oxidation-type reactions. Our earlier application Ser. No. 107,964, filed Dec. 28, 1978, discloses certain tin antimonate catalysts promoted with various different elements. Although these catalysts give good yields of the desired end products in various oxidation-type reactions, it is always beneficial to provide new catalysts having superior catalytic properties.

U.K. patent application GB2,009,613A, which was published on Jun. 20, 1979, was cited in the parent applications for its disclosure in Example 4 of an iron antimonate catalyst containing V, Mo, W, Te and Cu as promoters. Additionally, this patent further teaches that the catalysts described therein are useful in the known ammoxidation of propylene to acrylonitrile as practiced herein. As previously indicated, this reference, even though it is relevant to the ammoxidation process, fails to suggest the present invention in the sense of 35 USC 103 since there is no reasonable suggestion in the record that a promoter system effective in an iron antimonate catalyst would be expected to be similarly effective as a promoter system in a manganese antimonate catalyst.

Accordingly, it is an object of the present invention to provide new catalysts capable of providing superior yields of desired end products in various types of oxidation reactions.

SUMMARY OF THE INVENTION

These and other objects are accomplished by the present invention which is based on the discovery that certain manganese antimonate catalysts when promoted with certain combinations of elements provide excellent yields of desired end products such as, for example, acrylonitrile in various types of oxidation reactions.

Accordingly, the present invention provides new catalysts for use in various types of oxidation reactions, said catalysts comprising a manganese antimonate oxide complex of the formula:

$$A_aD_bC_cMn_dSb_eO_x$$

wherein:
A is at least one element selected from the group Cu, Ag, V, W and/or Mo;
D is at least one element selected from the group Te, Cr and/or Bi; D is preferably Te and/or Cr;
C is optional elements selected from the group Ti, Ge, Ce, La, Mg, Ca, Co, Ni, Nb, Ta, Zn, Cd, K, Cs, B, P and/or Eu; and wherein
a is 0.001 to 10;
b is 0.001 to 10;
c is 0 to 10;
d is 0.1 to 10;
e is 1 to 20, preferably 12; and
x is determined by the valence state of other elements.

In addition, the present invention provides improvements in the known processes for the oxidation of olefins to produce aldehydes and acids, the known processes for the ammoxidation of olefins to produce unsaturated nitriles, and the oxydehydrogenation of olefins to produce diolefins, the improvement in accordance with the invention comprising using as the oxidation catalyst a manganese antimonate oxide complex defined by the formula:

$$A_aD_bC_cMn_dSb_eO_x$$

wherein
A is at least one element selected from the group Cu, Ag, V, W and/or Mo; D is preferably Te and/or Cr;
D is at least one element selected from the group Te, Cr and/or Bi;
C is optional elements selected from the group Ti, Ge, Ce, La, Mg, Ca, Co, Ni, Nb, Ta, Zn, Cd, K, Cs, B, P and/or Eu; and wherein
a is 0.001 to 10;
b is 0.001 to 10;
c is 0 to 10;
d is 0.1 to 10;
e is 1 to 20, preferably 12; and
x is determined by the valence state of other elements.

DETAILED DESCRIPTION

The novel catalyst of the present invention finds significant use in various different reactions as described below.

AMMOXIDATION

A wide variety of different reactants can be ammoxidized in accordance with the present invention to produce nitriles. For example, olefins such as propylene and isobutylene, alcohols such as isopropanol, n-propanol, t-butyl alcohol, and aldehydes such as acrolein and methacrolein can be readily converted to nitriles in accordance with the present invention. In general, compounds which can be converted to nitriles by the inventive ammoxidation reaction include 3 to 9 carbon atom hydrocarbons unsubstituted or substituted with oxygen or hydroxyl, particularly olefins, aliphatic aldehydes, and mono-alakanols having 3-9 carbon atoms, usually 3-4 carbon atoms. Preferred starting materials are olefins, aldehydes and alcohols containing 3 or 4 carbon atoms.

The general ammoxidation process for converting olefins, alcohols and aldehydes to nitriles is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The inventive reaction is carried out in the same manner and under the conditions generally set forth in this patent.

In a preferred aspect, the inventive process comprises contacting a mixture comprising propylene or isobutylene, ammonia and oxygen with the promoted catalyst of this invention at an elevated temperature and at atmospheric or near atmospheric pressure.

Any source of oxygen may be employed in this process. For economic reasons, however it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hydrocarbons to the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e. in the range of 0.15:1 to 0.75:1. Above the upper limit of this range, the amount of aldehydes produced rapidly decreases. Within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are within the scope of the present invention and are preferred in fluid-bed operation.

In general, the molar ratio of added water to olefin, when water is added, is in the neighborhood of 0.1:1 or higher. Ratios on the order of 1:1 to 6:1 are particularly desirable, but higher ratios may be employed, i.e. up to about 10:1.

The reaction is carried out at an elevated temperature such as 200° C. to 600° C., preferably 400° C. to 500° C. The pressure at which the reaction is conducted is also an important variable, and the reaction should be carried out at about atmospheric or slightly above atmospheric (2 to 3 atmospheres) pressure. In general, high pressure, i.e. above 15 atmospheres, are not suitable since higher pressures tend to favor the formation of undesirable by-products.

The apparent contact time is not critical, and contact times in the range of from 0.1–40 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a vapor. Conventionally, this gaseous reaction product is treated to remove NH3 and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

OXIDATION

As previously indicated, the catalysts of this invention can also be employed in the catalytic oxidation of olefins to various different reaction products, such as unsaturated aldehydes and unsaturated acids.

The reactants used in the oxidation to oxygenated compounds are oxygen and an olefin such as propylene or isobutylene. Instead of such olefins, alcohols such as isopropanol, n-propanol or tert-butanol can be used as feeds.

The olefins or alcohols may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° C. to 600° C. may be advantageously employed. However, the process may be conducted at other pressures, and in the case where superatmospheric pressures, e.g. above 5 atmospheres are employed, somewhat lower temperatures are possible. In the case where this process is employed to convert propylene to acrolein, a temperature range of 200° C. to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired by-products and waste is diminished.

The apparent contact time employed in the process is not critical and it may be selected from a broad operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture of from 1:0.25 to 1:10 will give very satisfactory results while a ratio of 1:0.5 to 1:6 has been found the optimum when converting propylene to acrolein.

Inert diluents such as oxygen and carbon dioxide, may be present in the reaction mixture.

OXYDEHYDROGENATION

In accordance with the present invention, the promoted catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the promoted catalyst at a comparatively low temperature to obtain the corresponding diolefin.

By the term "olefin" as used in this reaction is meant open chain mono-olefins as well as cyclic mono-olefins. The olefins dehydrogenated in accordance with this invention have at least four and up to about nine non-quaternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methylbutene-1, 2-methylbutene-2, 3-methylbutene-1, 2-methylpentene-1, 3-methylpentene-2, 4-methyl-pentene-2; heptene-1; 3,4dimethyl-pentene-1; octene-1; cyclopentene; cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of mono-olefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 200° C. to about 800° C. Optimum yields are obtainable at temperatures within the range from about 300° C. to 600° C.

The preferred reaction pressure is approximately atmospheric, within the range of from about 0.1 to about 5 atmospheres.

Only a brief contact time with the catalyst is required for effective oxydehydrogenation. The apparent contact time with the catalyst can vary from about 0.1 up to about 50 seconds but higher contact times can be used if desired. At the short contact time, comparatively small reactors and small amounts of catalyst can be used effectively.

PROCESS CONDITION

In carrying out the foregoing processes, any apparatus of the type suitable for carrying out the oxidation reactions in the vapor phase may be employed. The processes may be conducted either continuously or intermittently. The catalyst may be a fixed-bed employing a large particulate or pelleted catalyst or, in the alternative, a fluid-bed catalyst may be employed which is micro-spheroidal.

CATALYST

The catalysts employed in accordance with the present invention are oxide complexes of manganese and antimony promoted with various additional elements and can be described by the following general formula:

$$A_aD_bC_cMn_dSb_eO_x$$

wherein
  A is at least one element selected from the group Cu, Ag, V, W and/or Mo;
  D is at least one element selected from the group Te, Cr and/or Bi;
  C is optional elements selected from the group Ti, Ge, Ce, La, Mg, Ca, Co, Ni, Nb, Ta, Zn, Cd, K, Cs, B, P and/or Eu; and wherein
  a is 0.001 to 10;
  b is 0.001 to 10;
  c is 0 to 10;
  d is 0.1 to 10;
  e is 1 to 20 preferably 12; and
  x is determined by the valence state of other elements.

The catalysts of this invention are substantially free of iron, uranium and tin, preferably completely free of these elements. By "substantially free" it is meant free other than amounts of impurities not purposely put in catalyst that do not materially affect the catalytic activity of the catalyst. Also, it is preferred that these catalysts contain at least two of the A elements, with the combination of Cu +W being especially preferred. Preferred catalysts are those in which C is 0.001 to 10. Preferably, C is selected from Ti, Ce, La, Mg, Co, Ni, Nb, Zn, K and Cs.

For all of the above catalysts, it is preferred that a is 0.5 to 5, preferably 0.1 to 2.5 based on 12 atoms of antimony, i.e. e is 12. In addition, it is preferred that the D/Sb ratio be within 0.1 to 2, preferably 0.3 to 1 based on 12 atoms of antimony (i.e. 0.1/12 to 2/12, preferably 0.3/12 to 1/12). Moreover, in all catalysts it is preferred that the Mn/Sb ratio is 1/5 to 1/1.1, more preferably ¼ to ½, most preferably about 1/3.

These catalysts can be used either in unsupported form or supported on suitable carriers such as $SiO_2$, $Al_2O_3$, $BPO_4$, $SbPO_4$, $ZrO_2$, $TiO_2$, Alundum and the like. The catalysts can also be coated on these supports by special techniques known in the art.

These catalysts can be prepared by conventional techniques such as disclosed in the previously mentioned U.S. Pat. No. 4,035,418.

EXAMPLES

In order to more thoroughly describe the present invention, the following working examples are presented. In these examples, the term "percent yield" means:

$$\frac{\text{moles product formed}}{\text{moles reactant fed}} \times 100$$

In each of the examples and comparative example, a catalyst having a composition set forth in the following table was prepared in accordance with a standard laboratory preparation. For example, the catalyst of Example 4 was prepared as follows:

94.09 gms. $Sb_2O_3$ was oxidized by heating in boiling aqueous $HNO_3$ for 24 hours. Next, 77.02 gms. of a 50 percent aqueous solution of $Mn(NO_3)_2$ was added to the antimony oxide slurry and the mixture refluxed for an additional 5 hours until the evolution of $NO_2$ had ceased. The slurry was then diluted with water and cooled and the pH adjusted to 6±0.2 with $NH_4OH$. The slurry was then filtered. To the filtrate were added individual aqueous solutions of the following components: 16.46 gms. $Cu(NO_3)_2 3 H_2O$, 3.42 gms. ammonium metatungstate, 12.20 gms. $Cr(NO_3\phi)_3 9H_2O$ and 77.02 gms. of a 50 percent aqueous solution of $Mn(NO_3)_2$. The mixture was stirred and then 75 gms. of a 40 weight percent silica sol was added. The resulting slurry was heated and stirred until thick and then dried at 120° C. with occasional stirring. The dried precatalyst was then heated in air at 290° C. for 3 hours and then at 425° C. for 3 hours to produce the desired catalyst.

EXAMPLES 1 TO 6 AND COMPARATIVE EXAMPLE

Six catalysts of the invention and a comparative catalyst were tested in the known ammoxidation reaction for producing acrylonitrile from propylene. In each example and comparative example, 5 cc. of the catalyst was charged into a 6 cc. reactor and contacted with a feed comprising 1 propylene/1.2 $NH_3$/10.5 air/4.0 water at 460° C. for a contact time of 6 seconds. Approximately one hour after initiation of the reaction product was recovered and analyzed.

The composition of the catalysts and the results obtained are set forth in the following table.

TABLE

| Ex. | Catalyst Compositions | HT (°C.) | Reaction Temp. (°C.) | Yields AN | HCN |
|---|---|---|---|---|---|
| Comp. | $Mn_{12}Sb_{36}O_x$ | 750 | 460 | 32.5 | 3.9 |
| 1 | $Cu_{1.27}W_{0.23}Bi_{0.57}Mn_4Sb_{12}O_x$ | 750 | 460 | 50.4 | 3.5 |
| 2 | $Cu_{1.27}Mo_{0.23}Te_{0.57}Mn_4Sb_{12}O_x$ | 750 | 460 | 64.8 | 4.2 |
| 3 | $Cu_{1.27}W_{0.23}Te_{0.57}Mn_4Sb_{12}O_x$ | 750 | 460 | 64.1 | 3.0 |
| 4 | $Cu_{1.27}W_{0.23}Cr_{0.57}Mn_4Sb_{12}O_x$ | 750 | 460 | 65.2 | 4.3 |
| 5 | $Cu_{1.27}W_{0.23}Cr_{0.57}Te_{0.17}Mn_4Sb_{12}O_x$ | 750 | 460 | 61.6 | 4.8 |
| 6 | $Cu_{1.27}W_{0.23}Te_{0.57}Cr_{0.17}Mn_4Sb_{12}O_x$ | 750 | 460 | 71.8 | 4.9 |

From the foregoing, it can be seen that the inventive catalyst provides significant yields of acrylonitrile when used in the conventional ammoxidation reaction. Thus, these catalysts are of significant commercial interest in this field. Moreover, these catalyst are also advantageous because they provide easy adjustment of the acrylonitrile/HCN yields ratio via minor compositional changes, they are redox stable and they provide an environmentally acceptable effluent (i.e. a by-product effluent with a very low COD).

EXAMPLE 7

In order to test catalysts of the invention in the known oxidation process for producing acrolein and acrylic acid from propylene, a feed comprising 1 propylene/10.6 air/4 $H_2O$ was contacted with 5 cc. of a catalyst comprising 80 percent $Cu_{1.27}W_{0.23}Te_{0.56}Cr_{0.17}Mn_4Sb_{12}O_x$ plus 20 percent $SiO_2$ at 400° C. for a contact time of 5 seconds. Acrolein was obtained in yields of 60.9 percent and acrylic acid obtained in yields of 1.8 percent for a total useful product yield of 62.7 percent.

EXAMPLE 8

Example 7 was repeated except that the feed comprised 1 propylene/9.7 air/4 $H_2O$ and the contact time was 10 seconds. Acrolein was recovered in yields of 61.5 percent and acrylic acid recovered in yields of 2.4 percent for a total useful product yield of 63.9 percent.

Although only a few embodiments of the present invention have been described above, it should be appreciated that many modifications can be made without departing from the spirit and scope of the invention. All such modifications are intended to be included within the scope of the present invention, which is to be limited only by the following claims.

We claim:

1. In an ammoxidation process in which oxygen, ammonia and a reactant selected from the group consisting of propylene and isobutylene in the vapor phase are contacted with a catalyst at elevated temperatures and a pressure of 14 or less atmospheres, the improvement wherein said catalyst comprises a manganese antimonate oxide complex of the formula:

$$A_aD_bC_cMn_dSb_{12}O_x$$

wherein
A is at least one of Cu, Ag, V, W and/or Mo;
D is Te and/or Cr;
C is optional elements selected from Ce, La, Mg, Ca, Co, Ni, Nb, Ta, Zn, Cd, K, Cs, B, P and/or Eu; and
wherein
a is 0.5 to 5;
b is 0.1 to 2;
c is 0 to 10;

d is 2.4 to 10; and x is determined by the valence requirements of the other elements present, and wherein A is selected so that said oxide complex at least contains Cu and at least one of Mo and W, and further wherein said oxide complex is substantially free of Fe, U, and Sn.

2. The process of claim 1 wherein C is at least one element selected from Ce, La, Mg, Co, Ni, Nb, Zn, K and/or Cs and further wherein c is at least 0.001.

3. The process of claim 1 wherein said catalyst contains W.

4. The process of claim 1 wherein said catalyst contains Mo.

* * * * *